United States Patent [19]

Butler et al.

[11] Patent Number: 4,665,258

[45] Date of Patent: May 12, 1987

[54] TOLUENE DISPROPORTIONATION PROCESS

[75] Inventors: James R. Butler; Kevin P. Menard, both of Big Spring, Tex.

[73] Assignee: Cosden Technology, Inc., Dallas, Tex.

[21] Appl. No.: 826,848

[22] Filed: Feb. 6, 1986

[51] Int. Cl.$^4$ ................................................ C07C 3/62
[52] U.S. Cl. .................................................... 585/475
[58] Field of Search ........................................ 585/475

[56] References Cited

U.S. PATENT DOCUMENTS 3,677,973  7/1972  Mitsche et al. ...................... 502/70
3,780,122  12/1973  Pollitzer .............................. 585/475

*Primary Examiner*—Curtis R. Davis
*Attorney, Agent, or Firm*—William D. Jackson; John K. Abokhair; M. Norwood Cheairs

[57] ABSTRACT

Process for the disproportionation of toluene employing an aluminum deficient mordenite catalyst. A toluene containing feedstock is supplied to a reaction zone containing a mordenite catalyst having a silica/alumina mole ratio of at least 30. The toluene WHSV is more than one. A hydrogen cofeed is supplied at a hydrogen/toluene mole ratio of 3-6, and the reaction zone is operated at a temperature within the range of 370°-500° C. and a hydrogen pressure of at least 500 psig. The toluene feedstock can have a moisture content in excess of 25 ppm and typically will have a water content ranging from about 50 ppm up to about the saturation point, about 250 ppm. A start-up procedure employs passing a hot preflush gas over the catalyst to dehydrate water from the catalyst prior to passing the toluene feedstock to the catalyst.

30 Claims, 8 Drawing Figures

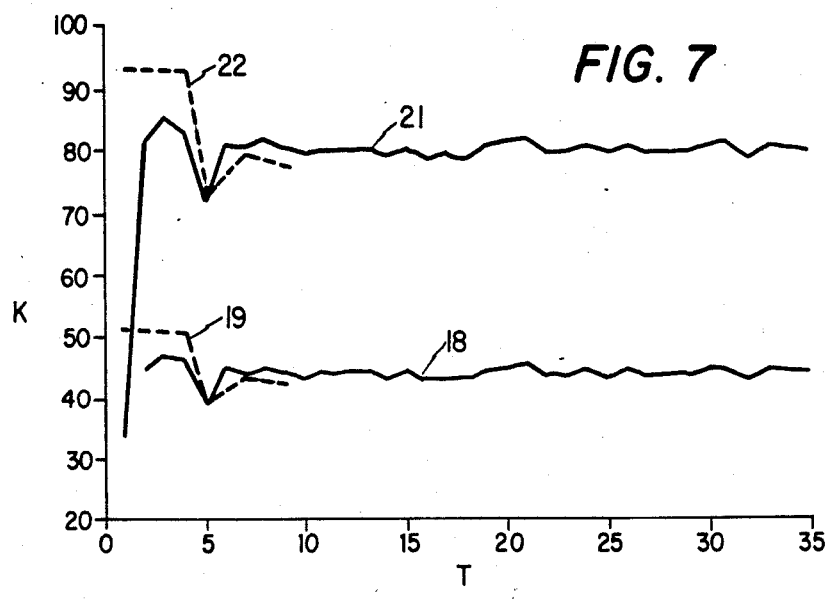
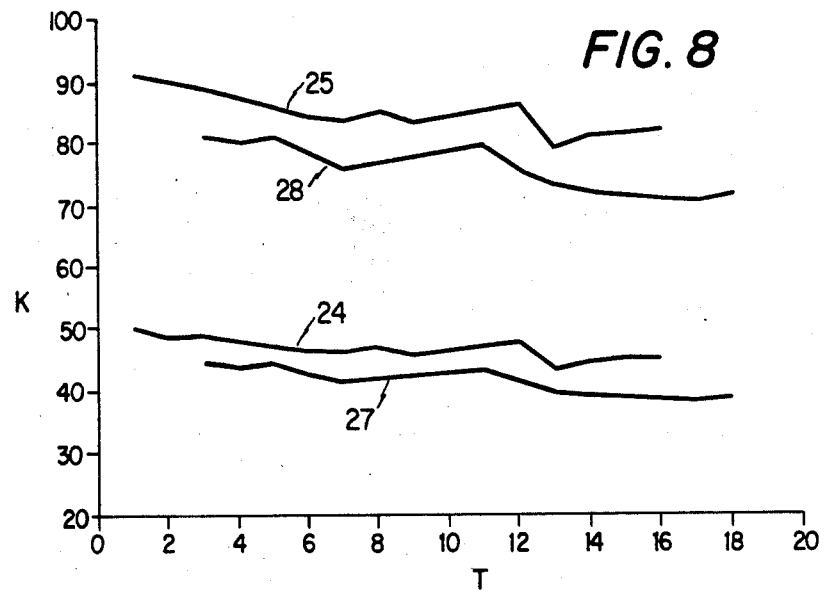

TOLUENE DISPROPORTIONATION PROCESS

TECHNICAL FIELD

This invention relates to the disproportionation of alkylaromatic feedstreams and more particularly to the disproportionation of toluene containing feedstocks employing mordenite catalysts of low aluminum content.

The disproportionation of toluene involves a well known transalkylation reaction in which toluene is converted to benzene and xylene in accordance with the following reaction:

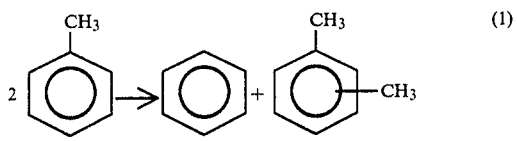

Reaction (1) is mildly exothermic.

Mordenite is one of a number of catalysts commonly employed in the transalkylation of alkylaromatic compounds. Mordenite is a crystalline aluminosilicate zeolite having a network of silicon and aluminum atoms interlinked in its crystalline structure through oxygen atoms. For a general description of mordenite catalysts, reference is made to Kirk Othmar *Encyclopedia of Chemical Technology*, 3rd Edition, 1981, under the heading "Molecular Sieves", Vol. 15, pages 638-643. Mordenite as found in nature or as synthesized, typically has a relatively low silica to alumina mole ratio of about 10 or less. Such conventionally structured mordenite catalysts are commonly employed in the disproportionation of toluene. However, mordenite catalysts having substantially lower alumina content are also employed in the disproportionation of toluene.

The disproportionation of toluene feed stocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art indicates that while relatively high temperatures can be employed for the high aluminum mordenites (low silica to alumina ratios) somewhat lower temperatures should be employed for the low alumina mordenites. For example, U.S. Pat. No. 3,527,826 to Sonoda et al discloses a process for the disproportionation of toluene employing a composite catalyst of at least 45 weight percent of a natural mordenite and no more than 55 weight percent of a synthetic mordenite, both in the acid (hydrogen) form. Here, the reaction temperature is said to be within the range of 300°-650° C. with 410°-500° C. being preferred.

Another process for the disproportionation of toluene, disclosed in U.S. Pat. No. 3,699,181 to Kmecak et al, employs a catalyst comprising a metal of Group VIB of the Periodic Table on a synthetic mordenite base. The synthetic mordenite, which has a normal alumina content, has a postulated formula of—$(Ca,Na_2) Al_2 Si_9O_{22}6H_2O$. Here relatively high temperatures are contemplated with the temperature range said to be between 700°-1100° F. and preferably between 800°-1000° F. In comparative tests with a type Y zeolite, the chromium mordenite catalyst was shown to be more selective at 850° F. than a type Y zeolite at 1000° F.

So called aluminum deficient mordenites, catalysts having a silica/alumina ratio greater than 10 and sometimes ranging up to 100, may also be used in the disproportionation of toluene. Low alumina mordenites may be prepared by direct synthesis as disclosed for example in U.S. Pat. No. 3,436,174 to Sand or by acid extraction of a more conventionally prepared mordenite as disclosed in U.S. Pat. No. 3,480,539 to Voorhies et al.

U.S. Pat. No. 3,780,122 to Pollitzer discloses the transalkylation of toluene using a mordenite zeolite having a silica/alumina ratio greater than 10 which is obtained by acid extraction of a mordenite zeolite having a silica/alumina ratio of less than 10. The silica/alumina ratio may range up to about 100 and preferably is at least about 15. The transalkylation conditions include a temperature within the range from about 200° C. to about 480° C. and a pressure ranging from about atmospheric to about 100 atmospheres. Specifically disclosed in Pollitzer are catalysts identified as catalysts A and B having silica to alumina ratios of about 15.5 and about 10.7, respectively.

In experimental work reported in Example II of this patent, the two catalysts were employed in a toluene transalkylation procedure for a duration slightly in excess of seven days. The lower ratio catalyst B was run at a temperature starting at 300° C. which was progressively increased over the life of the test to 400° C. For the higher ratio catalyst A, the temperature range was somewhat lower. It ranged from an initial value of 299° C. to a final value of 374° C.

While the higher ratio catalyst showed a somewhat greater activity than the other, neither catalyst showed good aging tolerance. Both lost about 15% activity in the first four days with some increase in activity occurring after that time. Whether the increase after the initial decrease in activity was due to an "edge" effect of the catalysts or because of the progressively increasing temperature conditions cannot be determined because of the short duration of the test.

The yield in the Pollitzer process is severely affected by water in the toluene feed stock. As shown in Table II, even a very small amount of water (15 ppm) reduces toluene conversion substantially.

Another process employing a mordenite containing catalyst in aromatic disproportionation reactions is disclosed in U.S. Pat. No. 3,677,973 to Mitsche et al. The reaction conditions are said to include a temperature ranging from 200° C. to about 480° C. and a pressure of about 1 atmospheric to 1500 psig. The catalyst employed includes about 60-90 weight percent low alumina mordenite composited with an alumina sol to provide a silica alumina ratio of the composite catalyst from about 10 to about 30. The specifically disclosed composite catalyst in Example I is 50% mordenite having a silica/alumina mole ratio of 19.7 and 42% alumina (to provide an overall silica/alumina ratio of about 10.7). This composite catalyst was employed in the transalkylation of toluene at reaction conditions of 420° C. and 500 psig.

Where mordenite catalysts of even higher silica/alumina ratios have been employed in the transalkylation of alkylaromatics, it has been the practice to operate at toward the lower end of the temperature range. It is also a common practice in this case to promote the catalyst with a catalytically active metallic content. Thus, U.S. Pat. No. 3,476,821 to Brandenburg et al discloses disproportionation reactions employing mordenite catalysts having a silica/alumina ratio within the range of 10–100 and preferably within the range of about 20–60. Here the desired temperature ranges are said to be from about 400°–750° F. and preferably 450°–640° F. Metal promoters were found to substantially increase activity and catalyt life. Without the addition of a metal promoter, the optimum silica/alumina ratio in terms of activity appears to be about 24 in tests run at 550° F., as reported in Example I. In Example III, a "product ratio" is presented as an indication of catalyst life. Mordenite having a silica/alumina mole ratio of 52 promoted with 5.2 weight percent nickel sulfide was shown to have a product ratio slightly less than that for mordenite of a silica/alumina mole rato of 24 when promoted with 0.4 weight percent platinum sulfide. Example V discloses comparative disproportionation runs carried out with mordenite of a silica/alumina mole ratio of 24:1 at temperatures of 550°–575° F. In run 1 with no added metal, catalyst activity decreased rapidly even under the mild disproportionation conditions employed. In runs 2 and 3, five weight percent nickel sufide was added to the catalyst and catalytic activity was extended although the tests were run for only a limited time (no more than 48 hours).

It is conventional practice to supply hydrogen along with toluene to the reaction zone. While the disproportionation reaction (1) is net of hydrogen, the use hydrogen cofeed is generally considered to prolong the useful life of the catalyst, as disclosed for example in the aforementioned patent to Brandenburg. The amount of hydrogen supplied, which normally is measured in terms of the hydrogen/toluene mole ratio, is generally shown in the prior art to increase as temperature increases. For example, while the aforementioned patent to Pollitzer discloses a range for the hydrogen/toluene ratio of 2–20 corresponding to the broad temperature range of 200°–480° C., the specific examples in Pollitzer of operating at temperatures ranging from 300°–400° C. employ a hydrogen/toluene mole ratio of 10.

The prior art, in addition to suggesting a dependent relationship between the hydrogen/toluene ratio and temperature, also indicates that the space velocities for toluene in the process become progressively lower as the aluminum deficiency (as indicated by the silica/alumina ratio) increases. Thus, Pollitzer while disclosing a very broad range of space velocities, a range of 0.1–20 hours$^{-1}$ in terms of liquid hourly space velocity (LHSV), employs space velocities for the aluminum deficient mordenite at the low end of this range. For example, in the experimental work reported in Pollitzer relating to the disproportionation of toluene, the process was operated at a weight hourly space velocity (WHSV) of 0.5 and a pressure of 500 psig.

The use of mordenite catalysts of high silica/alumina ratio in toluene disproportionation is also disclosed in U.S. Pat. No. 3,915,895 to Suggitt et al. The silica/alumina mole ratios proposed in Suggitt range from 10 to about 100 (preferably 12–80 and more preferably about 25 to 50). The catalysts for which experimental information is given in Suggitt had silica/alumina ratios of 18 and 39. At the disproportionation conditions employed (550° F. and 200 or 800 psig.), neither catalyst showed particularly good activity although the higher alumina catalyst promoted with silver was better than the unpromoted catalyst.

Bhavikatti et al, "Toluene Disproportionation over Aluminum-Deficient and Metal-Loaded Mordenites. 1. Catalytic Activity and Aging", Ind. Eng. Chem. Prod. Res. Dev. 1981, 20, 102–105, discloses toluene disproportionation at 400° C. over mordenite catalysts of silica/alumina mole ratios of 12, 16, 23, 32, and 61. The tests reported in Bhavikatti were carried out at atmospheric pressure and with a WHSV of 1. As the silica/alumina mole ratio is increased, catalyst activity substantially decreased while aging quality increased. That is, the aging rates were lower. Based upon short term aging studies, the best silica/alumina mole ratio appeared to be 23. Catalyst decay was also supressed by loading the mordenite with nickel.

The contraindication of high temperatures when employing high silica mordenites in toluene disproportionation is confirmed by the use of such mordenites in other reactions as disclosed in the aforementioned U.S. Pat. No. 3,480,539 to Voorhies et al. For example, in Table III of Voorhies, (column 6), catalyst J (silica/alumina mole ratio 69:1) had a somewhat better selectivity and activity for the designated reaction at 500° F. than did the normal mordenite, catalyst G, having a silica/alumina mole ratio of 10. However, when the temperature was increased to 550° F., the advantage derived from the highg silica alumina mole ratio was lost. Similarly, in FIG. 2 and Example II of the reference, catalyst H (silica/alumina mole ratio of 93) indicated a maximum activity for the indicated reaction at a temperature of about 500° F.

DESCRIPTION OF THE INVENTION

In accordance with the present invention, there is provided a new and improved process for the disproportionation of a toluene containing feed stock employing an alumina deficient mordenite catalyst under relatively severe disproportionation conditions. In carrying out one embodiment of the invention, the toluene containing feed stock is passed into a reaction zone and in contact with a mordenite catalyst therein having a silica/alumina mole ratio of at least 30. Preferably the catalyst has a silica/alumina ratio within the range of 40–60. The feed stock is supplied to the reaction zone at a rate to provide a toluene weight hourly space velocity (WHSV) greater than 1. Hydrogen is also supplied to the reaction zone at a rate to provide a hydrogen/toluene mole ratio within the range of 3–6. The reaction zone is operated at a temperature in the range of 370°–500° C. and a hydrogen pressure of at least 500° psig to effect disproportionation of the toluene to benzene and xylenes. In a preferred embodiment of the invention, hydrogen is supplied to the reaction zone in an amount to provide a mole ratio of hydrogen to toluene of about 4. Preferably the feed stock is substantially free of sulfur containing compounds. Preferred reaction conditions include a temperature within the range of 400°–480° C. and a pressure of about 600–800 psig. A preferred catalyst for use in the invention is hydrogen mordenite having a silica/alumina ratio of about 48.

In a further aspect of the invention, the toluene feed stock need not be subjected to a prior drying step before supplying it to the catalyst containing reaction zone. Thus, toluene feed stock having a water content in excess of 25 ppm can be applied directly into the reaction zone. In yet a further embodiment of the invention, a preflush gas is supplied to the reaction zone prior to initiating the disproportionation reaction. The preflush gas is heated to a temperature sufficient to strip water from the catalyst so that a substantially dehydrated catalyst is arrived at when the toluene feed is started. This enables the disproportionation process to be carried out initially at a somewhat lower temperature than would otherwise be the case without a sacrifice in toluene conversion. As the disproportionation process continues, the temperatures progressively increase to maintain the toluene conversion at the desired level, typically about 80% of theoretical.

BRIEF DESCRIPTION OF THE DRAWINGS

FIGS. 7 and 8 are graphs illustrating the effect of different start-up procedures on toluene conversion.

BEST MODES FOR CARRYING OUT THE INVENTION

Figure 1:
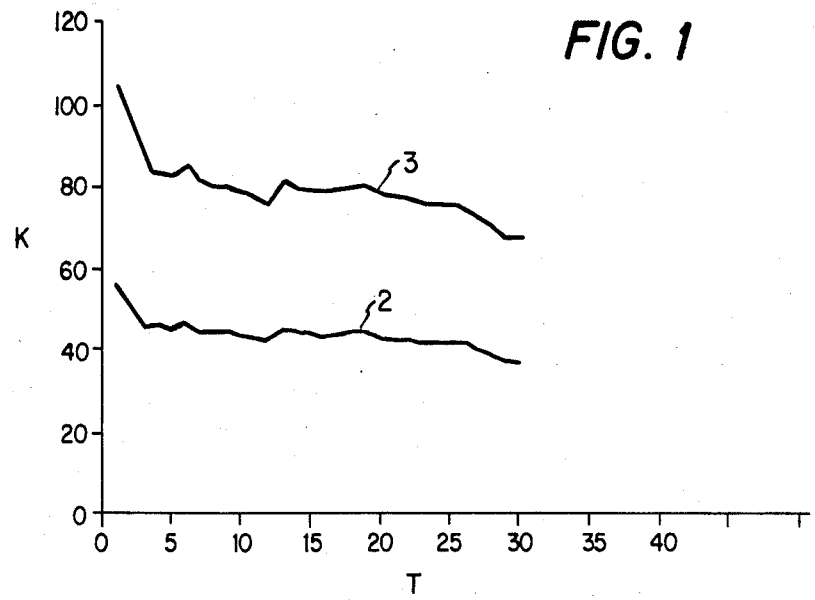
FIG. 1 is a graph illustrating toluene conversion in disproportionation processes employing an acid-leached aluminum deficient mordenite catalyst with silica/alumina ratio of 18.

As noted previously, it has been the practice in toluene disproportionation to employ alumina deficient mordenite catalysts under relatively mild disproportionation conditions. Usually the silica/alumina mole ratio of the catalyst is no more than 20 and the reaction temperature is less than about 400° C. and sometimes less than 300° C. Even then and particularly for temperatures above about 300° C. the normal procedure is to promote the catalyst with a metal as described in the aforementioned Suggitt and Brandenburg patents. Where it is desired to use higher temperatures up to about 550° C., the normal practice is to use lower silica/alumina ratio zeolites or to use more conventional acidic halide catalysts such as aluminum chloride.

In the present invention, aluminum deficient mordenites normally restricted for use in low temperature environments are employed in the disproportionation of toluene at relative high temperature conditions, specifically temperatures within the range of 370°–500° C. The mordenite catalyst employed in the present invention should have a silica/alumina ratio of at least 30. The catalyst need not be promoted. Hydrogen is normally also supplied to the reaction zone to provide a hydrogen pressure within the zone of at least 500 psig. Unless indicated otherwise, all pressures given herein are hydrogen pressures or in the case of a hydrogen feed containing other gases, hydrogen partial pressures. For example, in the case of a gas containing 90% hydrogen and 10% other gases such as light hydrocarbons and nitrogen, the reaction zone should be operated at a pressure of about 555 psig to yield a hydrogen presure of 500 psig. The pressure which the disproportionation reaction is carried out normally will be within the range of about 600–800 psig. Lower pressures may be employed, but will result in lower toluene conversion unless higher temperatures are used, which will decrease the catalyst cycle life. Preferably, the reaction zone for the toluene disproportionation reaction will be at a pressure of about 600 psig or above.

At the temperatures employed in the present invention and at the normal hydrogen pressure of 500 psig or more, the invention can be carried out under a combination of lower hydrogen requirements and higher space velocities than contemplated by the prior art. The specific parameters employed in this regard include a toluene space velocity (WHSV) in excess of 1 $hr^{-1}$ and a hydrogen/toluene mole ratio within the range of 3–6. Typical space velocities (WHSV) will range from about 1.3 to about 3 $hr^{-1}$. The experimental work reported herein was carried out at a WHSV of about 2.8 $hr^{-1}$ and actual plant operations described hereafter were carried out at space velocites ranging from about 1.3 to 2.3 providing toluene conversion at about 80% of theory. At those space velocities the nonaromatic product yield is primarily propane (about 1.5 volume percent).

While in theory hydrogen is not consumed in the disproportionation of toluene, in actual practice most toluene disproportionation operations do consume substantial quantities of hydrogen. In one commercial process hydrogen consumption is reported to be about 0.14 mols of hydrogen per mol of toluene and in another it is reported to be in excess of 0.3 mols of toluene per mole of hydrogen. In the present invention hydrogen consumption is less than 0.1 mol of hydrogen per mole of toluene. Thus the amount of hydrogen withdrawn from the reaction zone in relation to the amount of hydrogen cofeed is such as to provide an average consumption of less than 0.1 mol of hydrogen per mole toluene.

In experimental work carried out respecting the invention, mordenite catalysts of various silica/alumina mole ratios were tested to determine their activities in toluene disproportionation reactions and their aging characteristics in such reactions. Three catalysts identified herein as catalysts A, B and C were involved. The mordenite catalysts tested were in the acid (hydrogen) form. For catalyst A the silica/alumina mole ratio was 10, for catalyst B-18, and for catalyst C-48.

In terms of activity, catalyst B (silica/alumina ratio of 18) was significantly better than catalyst A and also slightly better than the higher silica mordenite, catalyst C. The activity for catalyst B was 46% as compared with 42% for catalyst A and 45% for catalyst C. In terms of aging quality of the catalyst, determined by the run time to reach a 5% loss in activity (as measured by toluene conversion), the more active catalyst B exhibited a better aging quality than catalyst A. Catalyst B ran for 22 days before a 5% loss in toluene conversion was observed as compared to 15 days for catalyst A. However, a very pronounced increase in aging quality was observed for the higher silica/alumina ratio catalyst C which, it will be recalled, exhibited a slightly lower activity than catalyst B. Here catalyst, C, having a silica/alumina mole ratio of 48 ran for 52 days before a 5% loss in toluene conversion was observed.

Figure 2:
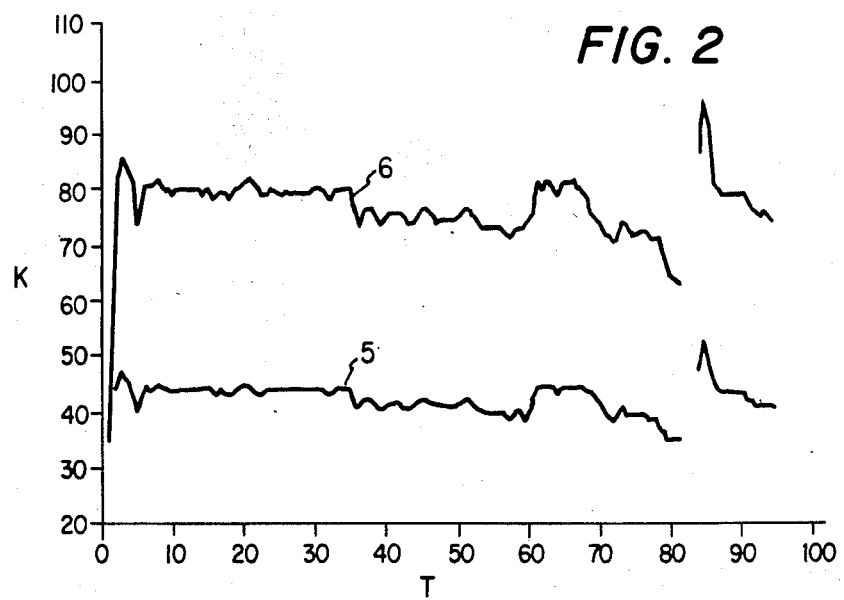
FIG. 2 is a graph showing toluene conversion for an aluminum deficient mordenite catalyst with a silica/alumina ratio of 48 under various pressure and temperature conditions.

Turning now to the drawings, FIGS. 1 and 2 are graphs of toluene conversion K plotted on the ordinate versus time T in days on the abscissa for catalysts B and C, respectively. In FIG. 1, curve 2 is a graph of absolute toluene conversion using catalyst B, expressed as a percentage of toluene in the feed, and curve 3 shows toluene conversion expressed as a percentage of total theoretical toluene conversion. As shown in FIG. 1, initial toluene conversion, once the run stabilized at about 3 days, was approximately 46%. It declined gradually thereafter until it reached the stage at which it had lost 5% of activity and shortly thereafter it declined more rapidly and the run was terminated. In the run depicted in FIG. 1, the hydrogen pressure in the reaction zone was maintained at approximately 600 psig and the average reaction temperature was 446° C. Hydrogen was supplied at a rate to provide a hydrogen/toluene mole ratio of 4.

In the experiment depicted in FIG. 2 employing catalyst C having a silica/alumina mole ratio of 48, the disproportionation reaction over the first sixty days was carried out at a pressure of 600 psig. and an average temperature measured at the inlet to the catalyst bed of 470° C. Percent toluene conversion absolute for this run is shown in FIG. 2 by curve 5 and toluene conversion expressed as a percent of theoretical conversions by curve 6. Here, once toluene conversion stabilized at about the sixth day, it remained relatively constant for thirty days and did not reach the point at which a 5% loss in activity occurred until day 52. Thus, catalyst C was substantially more resistant to aging than catalyst B even at the somewhat more severe disproportionation conditions (470° C. for catalyst C versus 446° C. for catalyst B).

At day 60 in this experiment, the hydrogen pressure was reduced to 400 psig. Toluene conversion fell off and the temperature was increased to 505° C. to compensate for the decrease in pressure and return the process to a toluene conversion level of about 44%. The activity of the catalyst remained stable for a few days but then began to decline sharply at about day 67, as shown by curves 5 and 6. At day 73, the temperature was increased to 525° C. and the run showed a slight increase in toluene conversion followed again by a relatively rapid deactivation of the catalyst. At day 82 the run was shut down and the catalyst was regenerated by bleeding air into a nitrogen stream which was flowed across the catalyst bed at atmospheric pressure and a temperature at 525° C. The initial regeneration stream contained 10% air in nitrogen for an initial period of about 4–6 hours. Thereafter the air concentration was increased until pure air was fed across the catalyst. After thus regenerating the catalyst for a period of about two days, the run was recommenced at day 84 at a pressure of 600 psig and a temperature of 460° C. The increased activity showed that the catalyst was successfully regenerated but activity again declined rapidly at the run temperature.

Figure 3:
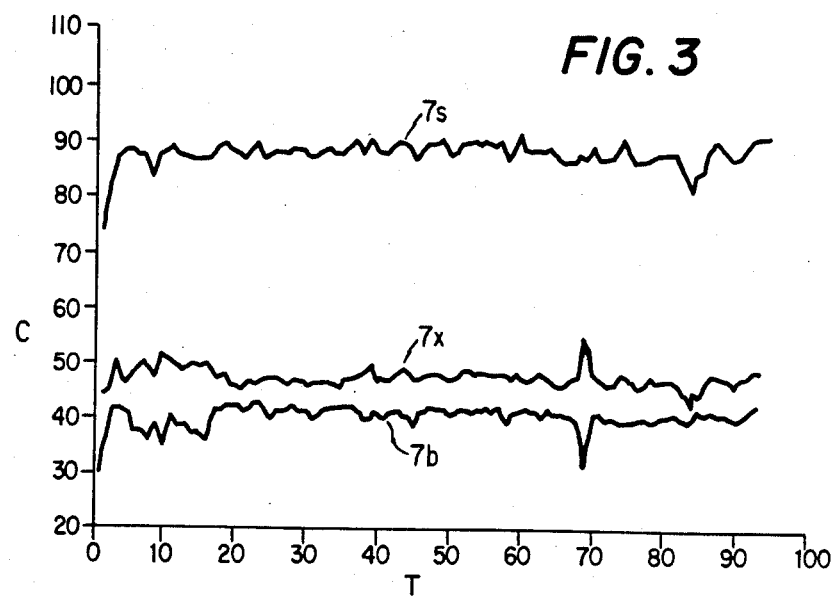
FIG. 3 is a graph illustrating the benzene and toluene production and total selectivity for the run depicted in FIG. 2.

The product makeup for the above experiment employing catalyst C is shown in FIG. 3. In FIG. 3, curves 7b and 7x are graphs of the percent concentrations C of benzene and xylene respectively in the effluent from the reaction zone on the ordinate against time T on the abscissa. The total selectivity of the process (the sum of the benzene and xylene makes) is also shown in FIG. 3 as curve 7s. As shown in FIG. 3, once the run stabilized, the total selectivity was very good, in excess of 85% and in some cases over 90%.

In the aforementioned experimental work, hydrogen was supplied to the reaction zone to provide a hydrogen/toluene mole ratio of 4.

Figure 4:
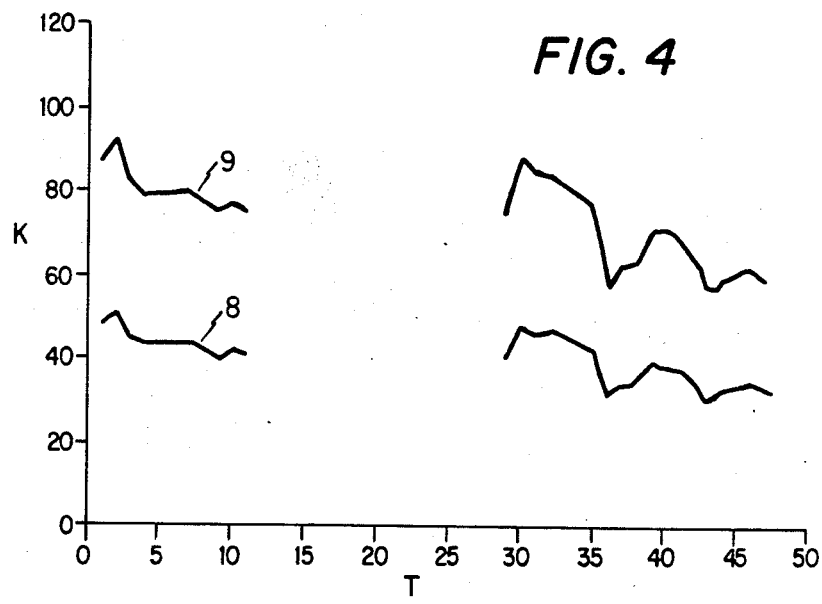
FIG. 4 is a graph showing the effect of hydrogen cofeed on toluene conversion.

The impact of hydrogen cofeed on the activity of catalyst C is illustrated in FIG. 4. In FIG. 4, curves 8 and 9 are graphs showing toluene conversion, K, on the ordinate versus time T in days on the abscissa expressed as percent absolute conversion and the percent of theoretical conversion, respectively. Throughout the run depicted in FIG. 4, the disproportionation conditions were 470° C. and 600 psig. For the initial 11 days the hydrogen/toluene mole ratio was maintained at 4. The experiment was then shut down and after being off for 17 days, it was recommenced and the hydrogen/toluene mole ratio of 4 was maintained for an additional eight days. At day 36, the ratio was reduced to 1. This resulted in a precipitous decline in toluene conversion. When the ratio was increased to 2:1 at day 38, toluene conversion increased to near its former level but then declined rapidly. At day 43, the hydrogen cofeed was increased to return to the original ratio of 4 and the run again appeared to stabilize.

It can be seen from the foregoing experimental work that hydrogen cofeed is desirable in terms of maintaining catalyst activity. When consideration is given to the silica/alumina ratio of the catalyst and the reaction conditions employed in the present invention, the hydrogen requirements are substantially less than would be expected in view of the prior art teachings. Thus, at the relatively high temperature conditions contemplated by the aforementioned patent to Sonoda, the preferred hydrogen/toluene mole ratio is said to be within the range of 8–20. For the temperature at which the experimental work in the aforementioned article by Bhavikatti were carried out (400° C.) the hydrogen/toluene mole ratio was 5 but the pressure was at atmospheric. While lower quantities of hydrogen have been employed in the prior art, these normally are associated with low temperature and pressure conditions. For example, in the aforementioned patent to Suggitt for a hydrogen/hydrocarbon mole ratio of 3, the reaction conditions for the disproportionation of toluene were 550° F. and 200 psig. The aforementioned patent to Pollitzer, while referring to a hydrogen/hydrocarbon mole ratio of 2 to 20 employs a hydrogen/toluene mole ratio of 10 even for the moderately aluminum deficient mordenite having a silica/alumina ratio of 15.7.

Figure 5:
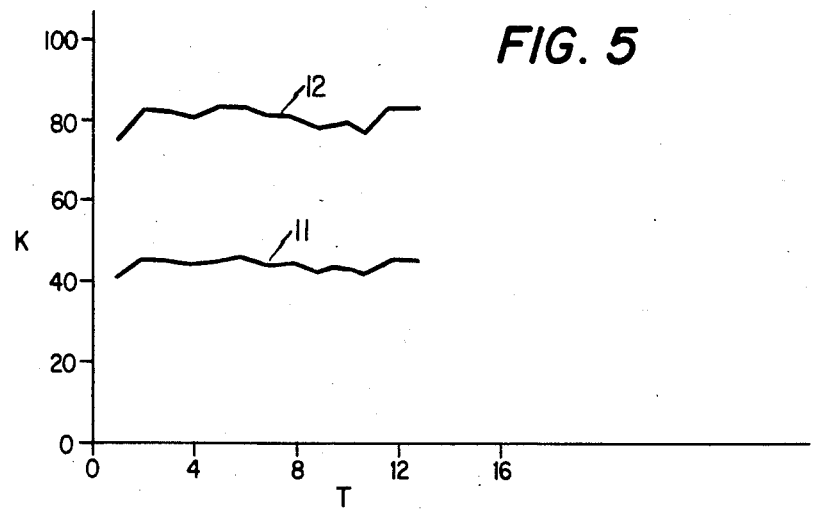
FIG. 5 is a graph illustrating the impact of water on catalyst activity.

As noted previously, the patent to Pollitzer teaches that toluene disproportionation over an aluminum deficient mordenite should be in a substantially water-free environment and thus the feed should be substantially anhydrous; less than 25 ppm water and preferably less than 10 ppm. Specifically, Pollitzer discloses that a very small increase in the amount of water (from 6 to 15 ppm) in the toluene feed substantially reduces toluene conversion after only a few hours or few days and designates an upper limit of 25 ppm. The present invention, on the other hand, is tolerant of water concentrations in the toluene feed above the 15 ppm concentration indicated by Pollitzer to be unsatisfactory and the 25 ppm upper limit in the Pollitzer process. The present invention can readily accommodate water concentrations ranging from about 50 ppm up to 250 ppm (saturation) encountered in toluene stocks under ambient atmospheric conditions. This is illustrated by experimental work and plant operations carried out employing catalyst C with toluene feed streams containing more than 100 parts per million by weight (PPM) water. One test was carried out with catalyst C and a toluene feed containing 143 ppm water at a pressure of 600 psig and a temperature throughout most of the test of 458°–470° C. Hydrogen cofeed was employed to provide a hydrogen/toluene mole ratio of 4. The results of this experiment are shown in FIG. 5 which is a graph of percent conversion K on the ordinance versus time T in days on the abscissa. In FIG. 5, curve 11 is absolute conversion and curve 12 is the toluene conversion expressed as a percentage of theory. As can be seen from an examination of FIG. 5 the catalyst showed only a slight loss of activity over the first 11 days. At day 12 the temperature was increased from about 458° C. to 470° C. and a corresponding increase in conversion was noted for the remaining two days of the run. Similar results in terms of catalyst aging quality have been observed in plant runs for a toluene feed stock containing about 200 ppm $H_2O$. The results here are in contrast to the disclosure in Pollitzer that much smaller quantities of water resulted in substantial diminution of catalytic activity after only a few days.

The above results should not be taken as an indication that substantial quantities of water should be added to the feed. In this respect, when steam was supplied as a cofeed in an amount of 18 volume percent based upon the toluene in the feed, the toluene conversion dropped from 83% to 23% of theoretical conversion after only one hour. Upon terminating steam cofeed for one hour, toluene conversion partially returned to 64% of theory. Thereafter cofeeding steam for 19 hours destroyed substantially all catalytic activity. Even after regeneration, toluene conversion went only to 60% of theory and it declined rapidly until the test was terminated.

Figure 6:
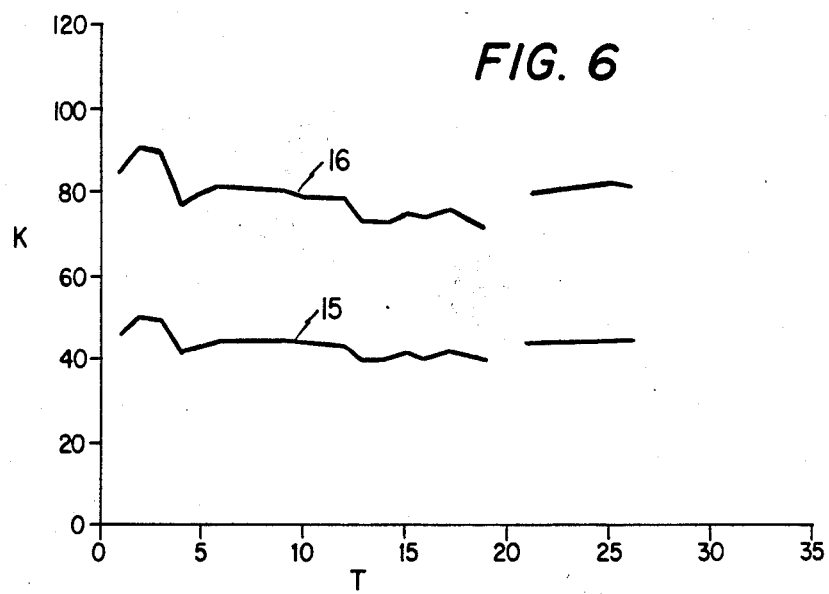
FIG. 6 is a graph illustrating the effect of hydrogen sulfide on toluene conversion.

Experimental work was also conducted to determine the effect of hydrogen sulfide upon toluene conversion in the disporportionation process of the present invention. The results of this experimental work are shown in FIG. 6 in which curves 15 and 16 are graphs of toluene conversion K absolute in percent and toluene conversion as a percent of theory, respectively versus time T in days. In this experiment, the nominal reaction temperature was 470° C., the hydrogen pressure 600 psig, and the hydrogen was fed along with the toluene to provide a hydrogen/toluene mole ratio of 4. The run was conducted in the conventional fashion until day 12, at which time hydrogen sulfide was added to the feed stream in an amount of 4 volume percent based upon the toluene. As shown by FIG. 6, the toluene conversion dropped rapidly then stabilized. At day 15, the hydrogen sulfide cofeed was terminated and the catalytic activity remained substantially flat showing only a small loss in activity. The run was terminated and the catalyst regenerated. The run was then started without hydrogen sulfide feed. The activity of the catalyst returned to the level observed prior to the initial charge of hydrogen sulfide to the catalyst bed.

As noted previously, it is a conventional practice to employ hydrogen as a cofeed in toluene disporportionation processes. The hydrogen is inert in the sense that as indicated by reaction (1), it is not a reactant and is not consumed in the disproportionation reaction. In a further embodiment of the invention, hydrogen or another similarly inert gas is employed in a start up procedure to precondition the catalyst beds prior to commencing toluene feed in the disporportionation process. The preconditioning procedure involves flowing hot inert gas through the catalyst bed. The result, as shown by the experimental work described hereinafter, is an increase in the initial activity of the catalyst permitting the process to be run at a somewhat lower temperature than would otherwise be the case.

The test results of the start-up procedure are reported in FIGS. 7 and 8 which present graphs of percent toluene conversion, K, plotted against time, T, in days. In the work depicted in FIG. 7, a first run was started in the normal manner by feeding toluene and hydrogen to the catalyst bed at a temperature of 470° C. In the second run, the test was started by passing a hydrogen stream at a temperature of 460° C. through the catalyst bed for 12 hours before starting the toluene feed. The results of these two runs are shown in FIG. 7 in which curves 18 and 19 show absolute toluene conversion for runs 1 and 2, respectively and curves 21 and 22 show toluene conversion as a percentage of theory for runs 1 and 2 respectively. Throughout run 2, which was terminated at the end of day 9, the temperature was maintained at 460° C. The reaction temperature during run 1 was 470° C.

Further tests conducted with respect to the startup procedure are illustrated FIG. 8. Here, nitrogen was employed as the preflush gas and both tests were carried out at the same temperature, 470° C. In FIG. 8, curves 24 and 25 represent toluene conversion absolute and as a percent of theory, respectively, for the case in which nitrogen flush was applied for 16 hours before starting the toluene feed. The nitrogen was heated to a temperature of 470° C. Curves 27 and 28 show the corresponding information for run 4 which was started up by direct feed of toluene and hydrogen to the catalyst bed. As indicated FIG. 7, the preflush step resulted in enhanced toluene conversion which continued throughout the duration of the test.

While this embodiment of the invention is not to be limited by theory, high silica/alumina ratio mordenites of the type employed in the present invention are hygroscopic and it is believed that the presence of water in the catalyst framework blocks some active sites. By passing the hot gas through the catalyst bed before the catalyst is exposed to toluene, the catalyst is dehydrated and more active sites are made available for the conversion reaction.

The duration of the preflush procedure and the temperature of the hot gas are interrelated with the higher temperatures permitting a shorter duration. As a practical matter it will usually be desirable heat the preflush gas to a temperature of at least 400° C. and to continue the preflush procedure for a period of at least 24 hours. Usually the preflush gas will simply be heated to approximately the same temperature as the feed stream during the conversion reaction. Higher temperatures should be avoided so as to not expose the catalyst to deactivating temperature conditions.

The invention has been employed in plant operations in the disproportionation of a toluene feed stream containing about 200 ppm water. In carrying out the process, hydrogen at a temperature of 316° C. was passed to the reactor containing catalyst C, described previously, for a period of 4.5 days. During the first day substantial quantities of water were recovered from the hydrogen effluent. The entrained water in the hydrogen effluent then decreased until the effluent gas was substantially dry, indicating substantially complete dehydration of the catalyst. Thereafter, toluene was supplied to the reactor at an initial rate of about 3000 barrels per day which was increased over a period of a week to about 5000 to 6000 barrels a day. After that, the average toluene charge to the reactor was maintained within the range of about 6000–8000 barrels per day.

Hydrogen was supplied to the reactor at a hydrogen/toluene mol ratio of about 4 and the hydrogen and the reactor operated at an inlet pressure ranging from about 620 to about 650 psig. The hydrogen feedstream had a purity of about 92% resulting in a hydrogen partial pressure within the reactor ranging from about 570–600 psig. The pressure gradient across the reactor from the inlet to the outlet was about 10 psi. The inlet temperature to the reactor was maintained within the range of 385° C. to about 395° C. during the first two weeks of operation and then progressively increased to the point where it was within the range of about 420-430 after about 8 weeks of operation. The upward temperature gradient through the reactor varied from about 10 to about 30° C.

During the first few days of start-up the space velocity was increased progressively from about 0.6 to about 1.3 WHSV. Once the process stabilized the average space velocities (WHSV) from about 1.4 to $2.3^{hr-1}$ were employed resulting in an average toluene conversion from about 80% of theory. The average hydrogen consumption over the course of the process was about 88 SCF/barrel of toluene corresponding to about 0.08 mol of hydrogen per mol of toluene.

Having described specific embodiments of the present invention, it will be understood that modifications thereof may be suggested to those skilled in the art and it is intended to cover all such modifications as fall within the scope of the appended claims.

We claim:

1. In a method for the disproportionation of a toluene containing feed stock to produce a disproportionation product containing benzene and xylene, the steps comprising:
   (a) passing said toluene feed stock into a reaction zone into contact with a mordenite catalyst within said reaction zone having a silica to alumina mole ratio of at least 30, said feed stock being supplied to said reaction zone at a rate to provide a tolune WHSV greater than 1;
   (b) supplying hydrogen to said reaction zone at a rate to provide hydrogen/toluene mole ratio within the range of 3-6;
   (c) carrying out the disproportionation reaction within said reation zone at a temperature within the range of 370°-500° C. and a hydrogen pressure of at least 500 psig; and
   (d) withdrawing said disproportionation product containing benzene and xylene from said reaction zone.

2. The method of claim 1 wherein said reaction zone is operated at a hydrogen pressure of at least 600 psig.

3. The method of claim 1 wherein hydrogen is supplied to said reaction zone in an amount to provide a hydrogen/toluene mole ratio of about 4.

4. The method of claim 1 wherein said mordenite catalyst has a silica/alumina mole ratio within the range of 40-60.

5. The method of claim 4 wherein said mordenite catalyst has a silica/alumina ratio of about 48.

6. The method of claim 5 wherein said reaction zone is operated at a pressure of at least 600 psig.

7. The method of claim 6 wherein said reaction zone is operated at a temperature of about 380°-480° C.

8. The method of claim 1 further comprising the step of prior to supplying said toluene feedstock said reaction zone, initiating a start up procedure by supplying a hot preflush gas to said reaction zone and flowing said hot gas into contact with said mordenite catalyst.

9. The method of claim 8 wherein said preflush gas is supplied to said reaction zone at a temperature of at least 400° C. for a period of at least 24 hours.

10. The method of claim 9 wherein upon initiating the flow of toluene feedstock to said reaction zone, said reaction zone is initially operated at a first relatively low temperature within the range of 370°-500° C. and subsequently operated at a second temperature within said range which is greater than said first temperature.

11. The method of claim 8 wherein said preflush gas comprises hydrogen.

12. The method of claim 8 wherein said preflush gas comprises nitrogen.

13. The method of claim 1 wherein hydrogen is withdrawn from said reaction zone in an amount in relation to the amount of hydrogen supplied to said reaction to provide an average hydrogen consumption in said reaction zone of less than 0.1 mole of hydrogen per mole of toluene.

14. In a process for the disproportionation of a toluene containing feedstock to produce a disproportionation product containing benezene and xylene, the steps comprising:
   passing the toluene feedstock having a water content in excess of 25 ppm into a reaction zone and into contact with a mordenite catalyst within said reaction zone having a silica to alumina mole ratio of at least 30;
   carrying out the disproportionation reaction within said reaction zone at a temperature within the range of 370°-500° C.; and
   withdrawing said disproportionation product containing benzene and xylene from said reaction zone.

15. The method of claim 14 wherein said toluene feedstock has a water content within the range of 50 ppm-250 ppm.

16. The method of claim 14 wherein hydrogen is supplied to said reaction zone and said disproportionation reaction is carried out at a hydrogen pressure of at least 500 psig.

17. The method of claim 16 wherein said reaction zone is operated at a hydrogen pressure of at least 600 psig.

18. The method of claim 14 wherein said feedstock is supplied to said reaction at a rate to provide a toluene WHSV greater than 1 and hydrogen is supplied to said reaction zone in an amount to provide a mole ratio of hydrogen to toluene of at least 4.

19. The method of claim 14 wherein said mordenite catalyst has a silica/alumina mole ratio within the range of 40-60.

20. The method of claim 19 wherein said mordenite catalyst has a silica/alumina ratio of about 48.

21. The method of claim 14 further comprising the step of prior to applying said toluene containing feedstock said reaction zone, initiating a start up procedure by supplying a hot preflush gas to said reaction zone and flowing said hot gas into contact with the mordenite catalyst to extract water from said catalyst.

22. The method of claim 21 wherein upon initiating the flow of toluene feedstock to said reaction zone, said reaction zone is initially operated at a first relatively temperature within the range of 370°-500° C. and subsequently operated at a second temperature within said range which is greater than said first temperature.

23. In a process for the disproportionation of a toluene containing feed stock to produce a disproportionation product containing benzene and xylene, the steps comprising:
   passing a preflush gas into a reaction zone containing a mordenite catalyst having a silica to alumina mole ratio of at least 30, said preflush gas being heated to temperature sufficient to dehydrate water from said catalyst;

withdrawing said preflush gas having water entrained therein from said reaction zone;

thereafter passing said toluene feed stock into said reaction zone and into contact with said mordenite catalyst; and carrying out the disproportionation reaction of toluene within said reaction zone at a temperature within the range of 370°–500° C., and withdrawing said disproportionation product containing benzene and xylene from said reaction zone.

24. The method of claim 23 wherein said disproportionation reaction is initially conducted within said reaction zone at a first relatively temperature and thereafter said temperature is progressively increased with time to values above said first temperature as said disproportionation reaction is carried out.

25. The method of claim 23 wherein hydrogen is supplied to said reaction zone and said dieproportionation reaction is carried out at a hydrogen pressure of at least 500 psig.

26. The method of claim 25 wherein said reaction zone is operated at a hydrogen pressure of at least 600 psig.

27. The method of claim 26 wherein said mordenite catalyst has a silica/alumina mole ratio within the range of 40–60.

28. The method of claim 27 wherein said mordenite catalyst has a silica/alumina ratio of about 48.

29. The method of claim 28 wherein said reaction zone is operated at a temperature of about 380°–480° C.

30. The method of claim 29 wherein said preflush gas comprises hydrogen.

* * * * *